(12) United States Patent
Carlino et al.

(10) Patent No.: US 6,489,467 B1
(45) Date of Patent: Dec. 3, 2002

(54) PROCESS FOR PURIFYING HIGH MOLECULAR WEIGHT HYALURONIC ACID

(75) Inventors: Stefano Carlino, Monthey (CH); François Magnette, Marsens (CH)

(73) Assignee: Chemedica S.A., Vouvry (CH)

( * ) Notice: Subject to any disclaimer, the term of this patent is extended or adjusted under 35 U.S.C. 154(b) by 0 days.

(21) Appl. No.: 09/868,529

(22) PCT Filed: Jan. 27, 2000

(86) PCT No.: PCT/IB00/00082

§ 371 (c)(1),
(2), (4) Date: Jun. 19, 2001

(87) PCT Pub. No.: WO00/44925

PCT Pub. Date: Aug. 3, 2000

(30) Foreign Application Priority Data

Jan. 28, 1999 (CH) ................................ 154/99

(51) Int. Cl.⁷ ............................ C07H 5/04; C07H 5/06; C08B 37/00
(52) U.S. Cl. ................... 536/55.3; 536/53; 536/55.1; 536/55.2; 514/54
(58) Field of Search ................. 536/53, 55.1, 55.2, 536/55.3; 514/54

(56) References Cited

U.S. PATENT DOCUMENTS 4,517,295 A  5/1985  Bracke

FOREIGN PATENT DOCUMENTS

EP  0266578 A  5/1988
EP  0694616 A  1/1996

*Primary Examiner*—Samuel Barts
*Assistant Examiner*—Michael C. Henry
(74) *Attorney, Agent, or Firm*—Clifford W. Browning; Woodard, Emhardt, Naughton, Moriarty & McNett

(57) ABSTRACT

A process for purifying high molecular weight hyaluronic acid from a biological source, including the steps of adjusting the pH of an aqueous solution containing high molecular weight hyaluronic acid from a biological source to a pH in the range from 1.7 to 3.3 and then diafiltering said aqueous solution at the same pH using a filter having a pore size in the range from 100,000 Daltons nominal molecular cut-off to 0.45 m, and of removing cells from the aqueous solution containing high molecular weight hyaluronic acid from biological source.

28 Claims, No Drawings

PROCESS FOR PURIFYING HIGH MOLECULAR WEIGHT HYALURONIC ACID

This application is the National Phase Application of PCT/1800/00082 filed Jan. 27, 2000.

The present invention relates to a process for purifying high molecular weight high molecular weight hyaluronic acid or a salt thereof.

Hyaluronic acid is a mucoid polysaccharide of biological origin, which is widely distributed in nature. For example, it is known that hyaluronic acid is present in various animal tissues such as umbilical cord, synovial fluid, vitreous humor, rooster comb and various connective tissues such as skin and cartilage.

Chemically, hyaluronic acid is a member of glycosaminoglycans and it is constituted by alternating and repeating units of D-glucuronic acid and N-acetyl-D-glucosamine, to form a linear chain having a molecular weight up to $13 \times 10^6$ Daltons.

In the meaning of the present invention, high molecular weight hyaluronic acid is hyaluronic acid having a molecular weight of not less than about $0.5 \times 10^6$ Daltons.

It is to be noted that the term "hyaluronic acid" in the present description and claims may mean indifferently hyaluronic acid in its acidic form or in its salt form such as for example sodium hyaluronate, potassium hyaluronate, magnesium hyaluronate, calcium hyaluronate, or others.

Hyaluronic acid, at high molecular weight, is viscous and able to maintain a jelly state, acting as a lubricant, preventing the invasion of bacteria and retaining water.

Due to these properties, hyaluronic acid is able to retain the tonicity and elasticity of the skin.

Pharmaceutical use of hyaluronic acid or of a salt thereof is widely described in the literature.

Since hyaluronic acid is a non-immunogenic substance and has viscoelastic and hydrophilic properties, it is used, since several years, as an eye vitreous or joint fluid replacement or as a supportive medium in ophthalmic surgery, as disclosed for example in U.S. Pat. No. 4,141,973 of Balazs.

In joint fluids, the viscous hyaluronic acid solution serves as a lubricant for to provide a protective environment to the cells, and for this reason, it is used in the treatment of inflamed knee joints.

EP-A-0 781 547 of Chemedica S.A. discloses a sodium hyaluronate based ophthalmic formulation for use in eye surgery.

EP-A-0 719 559 of Chemedica S.A. discloses sodium hyaluronate viscous solutions for use as masking fluid in therapeutic photokeratectomy by means of excimer laser.

EP-A-0 875 248 of Chemedica S.A. discloses the use of hyaluronic acid or of one of its pharmaceutically acceptable salts for the preparation of an aqueous solution useful as intra-articular lavage liquid.

EP-A-0 698 388 of Chemedica S.A. discloses an ophthalmic preparation for use as artificial tears containing hyaluronate as a viscosity thickener.

Thanks to its highly hydrophilic nature, hyaluronic acid may also be used in cosmetic products such as lotions and creams.

The pharmaceutical use of hyaluronic acid or of a salt thereof requires a highly pure product.

Hyaluronic acid can be extracted and purified for example from umbilical cords, from rooster combs or from group A and C Streptococci as disclosed for example in U.S. Pat. No. 4,141,973 of Balazs and U.S. Pat. No. 5,559,104 of Romeo et al.

Production of hyaluronic acid by Streptococci was first disclosed by Forrest et al. in 1937, (J. Biol. Chem. 118, 61 (1937)) and later it was demonstrated that hyaluronic acid from animal source is identical to hyaluronic acid from microbial source.

Processes for producing hyaluronic acid from microbial source are based on the property of Streptococci to have hyaluronic acid as the main component of their capsules.

Such microorganisms are able to transform the glucose present in their environment into D-glucuronic acid and N-acetyl-D-glucosamine and to produce hyaluronic acid as a secondary metabolite, to build their protective capsules.

The biosynthesis of hyaluronic acid by Streptococci is disclosed for example in U.S. Pat. No. 4,897,349 of Swann et al.

A number of processes are known for obtaining pharmaceutical grade hyaluronic acid or a sodium salt thereof from microbial sources.

For example, U.S. Pat. No. 4,780,414 of Nimrod et al., U.S. Pat. No. 4,517,295 of Bracke et al., and U.S. Pat. No. 5,563,051 of Ellwood et al. disclose processes for obtaining hyaluronic acid by continuous fermentation of Streptococcus bacteria and then purifying hyaluronic acid thus obtained up to pharmaceutical grade.

However, in all these processes, the purification of hyaluronic acid involves the precipitation of hyaluronic acid from microbial source by using large amounts of organic solvents such as ethanol, acetone, isopropanol, etc.

Some purifying processes are known wherein precipitation of hyaluronic acid from microbial source occurs by means of quaternary ammonium salts (U.S. Pat. No. 4,517,295 of Bracke et al.) or by means of anionic and cationic surfactants (U.S. Pat. No. 5,316,926 of Brown et al.).

However, the described procedures are quite complex and result in high production costs.

Some purifying processes are known wherein hyaluronic acid solution is diafiltered by using a filter having a nominal molecular weight cut-off of 10.000, 20,000 or 30,000 Daltons as disclosed for example in U.S. Pat. No. 5,563,051 of Ellwood et al. and U.S. Pat. No. 4,517,295 of Bracke et al.

However, due to the small nominal molecular weight cut-off used, these diafiltering procedures can be used only to discard small soluble molecules, and the diafiltered hyaluronic acid solution has to be treated by further processing in which various precipitation systems are involved, which render the whole purifying process complex.

An object of the present invention is to obtain a pharmaceutical grade high molecular weight hyaluronic acid or a salt thereof from any biological source, in particular from microbial sources, in high yield, at relatively low cost and preferably without the use of organic solvents or other added substances.

According to the present invention, this object has been achieved by a process for purifying high molecular weight hyaluronic acid from a biological source, characterized by:

a) a step of adjusting the pH of an aqueous solution containing high molecular weight hyaluronic acid from a biological source to a pH in the range from 1.7 to 3.3 and then diafiltering said aqueous solution at the same pH using a filter having a pore size in the range from 100,000 Daltons nominal molecular weight cut-off to 0.45 $\mu$m;

b) a step of removing cells from the aqueous solution containing high molecular weight hyaluronic acid from biological source, said step being carried out either before step a) or after step a);

c) a step of sterilization.

Advantageously, by means of a process including a step of diafiltration at a pH in a range of 1.7 to 3.3 and a step of removing cells it is possible to purify high molecular hyaluronic acid so as to obtain in high yield a pharmaceutical grade high molecular weight hyaluronic acid or a salt thereof from any biological source and in particular from a microbial source.

According to step a) of the process of the present invention, hyaluronic acid is diafiltered at a nominal molecular weight cut-off or pore size which allows the returning of the hyaluronic acid and the passing through the filter of all substances contained in the solution or broth.

The process of the present invention may be carried out by using any biological source of hyaluronic acid.

Advantageously, pharmaceutical grade hyaluronic acid may be obtained by the process of the present invention without traces of organic solvents or other added substances, since in the purifying process of the present invention, hyaluronic acid is not precipitated with organic solvents or other substances, but is maintained in aqueous solution during the whole process.

Other objects, characteristics and advantages of the present invention become apparent from the following detailed description.

Hyaluronic acid from any biological source may be purified up to a pharmaceutical grade by the process of the present invention.

For example, the aqueous hyaluronic acid solution containing high molecular weight hyaluronic acid which is firstly treated, either according to step a) of the present invention, or according to step b) of the present invention, may be an aqueous solution containing high molecular weight hyaluronic acid obtained by extraction from umbilical cord, rooster comb or others.

However, in a preferred embodiment of the invention, the aqueous hyaluronic acid solution which is firstly treated, either according to step a), or according to step b), is an aqueous broth containing high molecular weight hyaluronic acid from microbial source.

The microbial source is preferably a Streptococcus species producing high molecular weight hyaluronic acid, and more preferably the microbial source is selected from *Streptococcus zooepidemicus, Streptococcus equi* and *Streptococcus pyogenes*.

A broth containing high molecular weight hyaluronic acid may be prepared by any well-known process including fermentation of a Streptococcus culture producing high molecular weight hyaluronic acid in an appropriate aqueous medium and under appropriate conditions. Such processes are disclosed for example in U.S. Pat. No. 4,780,414 of Nimrod et al., U.S. Pat. No. 5,563,051 of Ellwood et al. or U.S. Pat. No. 5,316, 916 of Brown et al.

The process for preparing an aqueous broth containing high containing high molecular weight hyaluronic acid according to the present invention may be the following, by way of example:

At the end of an usual fermentation process, the broth containing hyaluronic acid, having a pH of about 7.4, is harvested and transferred into a tank equipped with automatic temperature control.

The temperature is maintained at a value in the range from 15° C. to 25° C., preferably, at 20° C.

The aqueous hyaluronic acid solution or broth thus obtained may then be treated according to the purifying process of the present invention.

The diafiltration, according to step a) of the present invention, of a solution of hyaluronic acid from a biological source at a pH in the range from 1.7 to 3.3, using a filter having a pore size in the range from a 100,000 Daltons nominal molecular weight cut-off to 0.45 $\mu$m, leads to the removal of all proteins and other soluble materials present in the aqueous solution.

It is assumed that when the pH of a hyaluronic acid solution is adjusted in the range from 1.7 to 3.3, a kind of reversible cross-linkage occurs, in which the molecules of hyaluronic acid form a network which may be broken under other pH conditions.

In the range of pH from 1.7 to 3.3, the network is able to be retained by the filter having a pore size in the range from a 100,000 Daltons nominal molecular weight cut-off to 0.45 $\mu$m, while proteins and other materials pass through the filter, thereby making it possible to separate hyaluronic acid from any soluble substances contained in the solution.

In step a), the pH of the aqueous solution is preferably adjusted to a value in the range from 2.0 to 2.7 and then this solution is diafiltered at the same pH.

More preferably, in step a), the pH of the aqueous solution is adjusted to a value in the range from 2.3 to 2.7 and then this solution is diafiltered at the same pH.

In step a), the pH is preferably adjusted by means of an HCl aqueous solution.

In a first preferred embodiment of the process of the invention, wherein step b) of removing cells is carried out after diafiltration step a), the pH of the aqueous hyaluronic acid solution or broth obtained from a biological source is first adjusted to a value in the range from 1.7 to 3.3, preferably to 2.5–2.6, preferably with an HCl aqueous solution.

At this pH, the aqueous hyaluronic acid solution or broth is transformed into a very viscoelastic aqueous solution or broth containing high molecular weight hyaluronic acid in a network arrangement.

The aqueous solution or broth containing high molecular weight hyaluronic acid thus obtained is then diafiltered, preferably according to a cross flow diafiltration process, while maintaining the same pH during the whole diafiltration step.

In step a) of the purifying process according to said first preferred embodiment, a filter particularly preferred has a pore size of 0.2 $\mu$m.

In said diafiltration step a), the viscoelastic aqueous solution or broth containing high molecular weight hyaluronic acid is pumped into a cross flow filter holder equipped with suitable number of filter cartridges having a pore size in the range from a 100,000 Daltons nominal molecular weight cut-off to a 0.45 $\mu$m pore size, preferably a 0.2 $\mu$m pore size and pyrogen free distilled water is then added in the tank containing the viscoelastic aqueous solution containing high molecular weight hyaluronic acid, at the same flow rate as the outgoing filtrate, in order to maintain a constant volume.

In step a) of the purifying process according to said first preferred embodiment, the viscoelastic aqueous solution or broth containing high molecular weight hyaluronic acid is preferably diafiltered until the filtrate which is discarded has an optical density (OD) at a wavelength of 280 nm equal to or lower than 0.02. In this case, the optical density of the filtrate at this wavelength should be monitored during the entire diafiltration process.

According to said first preferred embodiment, the step a) of diafiltration is followed by a step b) of removing cells, preferably a step b) of centrifugation in order to remove any cells or proteins still present in the diafiltered solution or broth.

In case of microbial source, the step of centrifugation may comprise for example adjusting the pH of the diafiltered broth to a pH in the range from 3.5 to 5.0, preferably to 4.0, and then centrifuging the diafiltered aqueous broth, thus obtaining a supernatant containing high molecular weight hyaluronic acid.

Preferably, the pH of the diafiltered broth is adjusted by means of an aqueous NaOH solution. However, other basic aqueous solutions could be used.

According to said first preferred embodiment, the step b) of removing cells is followed by a step of sterilization c).

According to a second preferred embodiment of the process of the invention, step b) of removing cells is carried out before diafiltration step a).

In said second preferred embodiment, the step b) of removing cells is preferably a cross flow diafiltration step of removing cells.

In said diafiltration step of removing cells b), the pH of the aqueous hyaluronic acid solution or broth obtained from biological source is first adjusted to 3.5, preferably with an HCl aqueous solution, and then the thus obtained aqueous solution or broth is diafiltered at the same pH using a filter having a pore size of 0.2 µm.

In said diafiltration step b) of removing cells, the aqueous solution or broth containing high molecular weight hyaluronic acid is pumped into a cross flow filter holder equipped with suitable number of filter cartridges having a pore size of 0.2 µm and sterile pyrogen free distilled water is then added in the tank containing the aqueous solution or broth containing high molecular weight hyaluronic acid, at the same flow rate as the outgoing filtrate, in order to maintain a constant volume.

At this pH, the filter having the pore size of 0.2 µm allows the returning of the cells and the passing through the filter of hyaluronic acid.

In step b) of the purifying process according to said second preferred embodiment, the aqueous solution containing high molecular weight hyaluronic acid is preferably diafiltered until 10 equivalent volumes of sterile pyrogen free distilled water was added.

In step a) of said second preferred embodiment, the pH of the aqueous hyaluronic acid solution essentially free of cells obtained in step b) is first adjusted to 1.7 to 3.3, preferably to 2.4, preferably with an HCl aqueous solution.

At this pH, the aqueous hyaluronic acid solution is transformed into a very viscoelastic aqueous solution containing high molecular weight hyaluronic acid in a network arrangement.

The aqueous solution containing high molecular weight hyaluronic acid thus obtained is then diafiltered, preferably according to a cross flow process, while maintaining the same pH during the whole diafiltration step.

In step a) of the purifying process of the present invention according to said second preferred embodiment, a filter particularly preferred has a 300.000 D nominal molecular weight cut-off.

In said diafiltration step a), the viscoelastic aqueous solution containing high molecular weight hyaluronic acid is preferably pumped into a filter holder equipped with suitable number of filter cartridges having a pore size in the range from a 100,000 Daltons nominal molecular weight cut-off to a 0.45 µm pore size, preferably 300.000 D nominal molecular weight cut-off and concentrated, and sterile pyrogen free distilled water is then added in the tank containing the concentrated viscoelastic aqueous solution containing high molecular weight hyaluronic acid, at the same flow rate as the outgoing filtrate, in order to maintain a constant volume.

In step a) of the purifying process of the present invention according to said second preferred embodiment, the viscoelastic aqueous solution containing high molecular weight hyaluronic acid is preferably diafiltered until 15 equivalent volumes of sterile pyrogen free distilled water was added. The filtrate is discarded.

By applying said second preferred embodiment, a centrifugation is advantageously avoided.

According to said second preferred embodiment, the step a) of diafiltration is followed by a step of sterilization c).

The step of sterilization according to the present invention is preferably a filtering sterilization step.

In the present invention, the filtering sterilization may be carried out according to a standard filtering sterilization method.

According to said first preferred embodiment, the filtering sterilization step is carried out by adjusting the pH of the supernatant obtained in the step b) of centrifugation to a value of 7.0 and then filtering the supernatant through a filter having a pore size of 0.2 µm.

According to said second preferred embodiment, the filtering sterilization step is carried out by adjusting the pH of the diafiltered solution containing hyaluronic acid obtained in step a) to a value of 7.0 and then filtering the solution through a filter having a pore size of 0.2 µm.

In these two preferred embodiments, the pH is preferably adjusted by means of an aqueous NaOH solution. However, other basic aqueous solutions could be used.

Then, the sterile solution may be concentrated by using a filter having a 5,000–10,000 Daltons nominal molecular weight cut-off.

After concentration, the sterilized solution may be finally freeze dried to obtain a dry powder of hyaluronic acid or of a salt thereof.

The hyaluronic acid or a salt thereof obtained by the purifying process according to the present invention has a pharmaceutical grade and the yield is about 70–90% by weight with regard to the hyaluronic acid content in the crude solution.

The hyaluronic acid or salt thereof obtained by the purifying process of the present invention is remarkable by the absence of pyrogenicity and inflammatory activity.

The hyaluronic acid or salt thereof obtained by the purifying process of the present invention contains between 90% and 95% by weight of hyaluronic acid consisting of D-glucuronic acid and N-acetyl-D-glucosamine in a ratio of 1:1, from about 3% to 5% by weight of water, less than 0.2% by weight of proteins, less than 0.3% by weight of nucleic acids and less than 0.3% by weight of neutral sugar.

The process of the present invention is very simple and very advantageous from economical and ecological points of view since no other substance than HCl or NaOH are involved.

When the purifying process of the present invention is being used, the hyaluronic acid or salt thereof contains no trace of organic solvents.

The following examples of the process for obtaining pharmaceutical grade high molecular weight hyaluronic acid or a salt thereof according to the present invention are given for illustrative purposes only and are not intended to limit the scope of the invention.

EXAMPLES

Preparation of an Aqueous Broth Containing High Molecular Weight Hyaluronic Acid from Microbial Source Cells of *Streptococcus equi* were cultivated at a temperature 37° C. in an appropriate medium composed of:

| | |
|---|---|
| Glucose | 60 g |
| Soytone | 15 g |
| Yeast extract | 5 g |
| Monobasic potassium phosphate | 2.5 g |
| Magnesium sulfate eptahydrate | 1.2 g |
| Purified and pyrogen free water | 1 lt |

Ten liters of this medium were sterilized and inoculated with a 1–2% Streptococcus equi culture having an optical density (OD) of about 7 measured at a wavelength of 650 nm.

During fermentation, the pH of the broth was automatically maintained at 7.4 by addition of NaOH 5 N. The aeration was kept at 1 volume of air per volume of medium per minute, and the agitation was maintained at 250 rpm during the whole fermentation period.

After 20 hours, the broth was harvested and transferred into a suitable tank with a volume capacity of 50 liters.

Purifying Process According to a First Preferred Embodiment of the Present Invention.

Under continuous agitation, the pH of the broth as prepared above was adjusted to 2.5 with HCl 6 N, thus obtaining a very viscous broth which appears as a thick blob.

The aqueous broth was then pumped in a cross flow filter holder, equipped with three 0.2 μm filter cartridges disposed one upon the other. The filter used is a SARTOCON cassette, Mod. No. 302 186 07 06 W-SG manufactured by SARTORIUS having a pore size of 0.2 μm.

At the beginning of the feeding of the aqueous broth into the filter, the filtrate valve was maintained closed in order to recirculate the aqueous broth for several minutes, until the system was stable and no bubbles were present in the retentate.

The filtrate valve was then opened, and sterile pyrogen free distilled water was added continuously in the tank containing the aqueous broth, at the same flow rate as the outgoing filtrate, in order to maintain constant the volume of the aqueous broth. The inlet pressure is maintained in the range from 1 to 3 bars, preferably at 2 bars.

The diafiltration was stopped when the absorbance of the filtrate at a wavelength of 280 nm was 0.012 OD. The filtrate was discarded.

The pH of the diafiltered broth was then adjusted to 4 with NaOH 5 N and thereupon the broth was centrifuged at 9,000 rpm and at 15° C. with a refrigerated centrifuge.

The pH of the supernatant was then adjusted to a pH of 7.0 with NaOH 5 N and the solution was filtrated through a filter having a 0.2 μm pore size, so as to sterilize the solution, according to a standard filtering sterilization method.

The sterile solution was then freeze dried according to a standard freeze dried process in order to obtain a dry powder of sodium hyaluronate.

In this example, the yield in hyaluronic acid was about 85–87% with regard to the hyaluronic acid content in the crude solution and the product had the following characteristics:

sodium hyaluronate content . . . 96.5%
   intrinsic viscosity (25° C.)=2100 ml/gr (corresponding to a molecular weight of $1.7 \times 10^6$ Daltons)
water content . . . 3.1%
protein content . . . 0.08%
nucleic acid content . . . 0.01%
neutral sugar content . . . 0.01%

The thus obtained high molecular weight sodium hyaluronate may be used for preparing pharmaceutical compositions.

Purifying Process According to a Second Preferred Embodiment of the Present Invention.

Under continuous agitation, the pH of 5 liters of the aqueous broth containing high molecular hyaluronic acid from microbial source as prepared above was adjusted to 3.5 with HCl 6N and maintained at this level during the whole cross flow diafiltration step of removing cells.

The aqueous broth (5 liters) was then pumped in a cross flow filter holder, equipped with three 0.2 μm filter cartridges disposed one upon the other. The filter used is a SARTOCON cassette, Mod. No. 302 186 07 04 O-SG manufactured by SARTORIUS having a pore size of 0.2 μm.

At the beginning of the feeding of the aqueous broth into the filter, the filtrate valve was maintained closed in order to recirculate the aqueous broth for several minutes, until the system was stable and no bubbles were present in the retentate.

The filtrate valve was then opened, and 10 equivalent volumes of sterile pyrogen free distilled water was added continuously in the tank containing the aqueous broth, at the same flow rate as the outgoing filtrate, in order to maintain constant the volume of the aqueous broth. The inlet pressure is maintained in the range from 1 to 3 bars, preferably at 2 bars.

The retentate was discarded and the filtrate (50 liters) containing high molecular weight hyaluronic acid free of cells was further treated.

The pH of the diafiltrated solution (50 liters) containing hyaluronic acid thus obtained was thereafter adjusted to 2.4, thus obtaining a very viscous solution, and maintained at this level during the whole cross flow diafiltration process.

The aqueous broth (50 liters) was then pumped in a cross flow filter holder, equipped with three 300.000 D filter cartridges disposed one upon the other. The filter used is a SARTOCON cassette, Mod. No. 302 146 790 07 7E-SG manufactured by SARTORIUS having a pore size of 300.000 D.

At the beginning of the feeding of the aqueous broth into the filter, the filtrate valve was maintained closed in order to recirculate the aqueous broth for several minutes, until the system was stable and no bubbles were present in the retentate.

The filtrate valve was then opened, and the aqueous broth was then concentrate to reduce the volume to 7.5 liters. The filtrate (42.5 liters) was discarded.

Then, 15 equivalent volumes of sterile pyrogen free distilled water was added continuously in the tank containing the aqueous broth, at the same flow rate as the outgoing filtrate, in order to maintain constant the volume of the aqueous broth. The inlet pressure is maintained in the range from 1 to 3 bars, preferably at 2 bars. The filtrate (116 liters) was discarded.

The feeding of water was then stopped and the aqueous broth was concentrated.

The pH of the concentrated diafiltered solution (4 liters) was then adjusted to a pH of 7.0 with NaOH 5N and the solution was filtered through a static filter having a 0.2 μm pore size, so as to sterilize the solution, according to a standard filtering sterilization method.

The sterile solution was then freeze dried according to a standard freeze dried process in order to obtain a dry powder of sodium hyaluronate.

In this example, the yield in hyaluronic acid was about 83–85% with regard to the hyaluronic acid content in the crude solution and the product had the following characteristics:

sodium hyaluronate content . . . 97.0%
   intrinsic viscosity (25° C.)=2100 ml/gr (corresponding to a molecular weight of $1.7\text{--}10^6$ Daltons)

water content . . . 2.9% protein content . . . 0.08% nucleic acid content . . . 0.01% neutral sugar content . . . 0.01%

The thus obtained high molecular weight sodium hyaluronate may be used for preparing pharmaceutical compositions.

What is claimed is:

1. A process for purifying high molecular weight hyaluronic acid from a biological source in order to obtain pharmaceutical grade high molecular weight hyaluronic acid or a salt thereof, characterized in that it comprises:
   a) a step of adjusting the pH of an aqueous solution containing high molecular weight hyaluronic acid from a biological source to a pH in the range from 1.7 to 3.3 and then diafiltering the solution at the same pH using a filter having a pore size in the range from 100,000 Daltons nominal molecular weight cut-off to 0.45 $\mu$m;
   b) a step of removing cells from the aqueous solution containing high molecular weight hyaluronic acid from biological source, said step being carried out either before step a) or after step a);
   c) a step of sterilization.

2. The process according to 1, characterized in that the aqueous solution containing high molecular weight hyaluronic acid from a biological source which is firstly treated, either according to step a) or according to step b) is an aqueous broth containing high molecular weight hyaluronic acid from microbial source.

3. The process according to claim 2, characterized in that the microbial source is a Streptococcus species producing high molecular weight hyaluronic acid.

4. The process according to claim 3, characterized in that the Streptococcus species producing high molecular weight hyaluronic acid is selected from *Streptococcus zooepidemicus, Streptococcus equi* and *Streptococcus pyogenes.*

5. The process according to claim 1, characterized in that in step a), the pH of the aqueous solution containing high molecular weight hyaluronic acid is adjusted to a value in the range from 2.0 to 2.7 and then the solution is diafiltered at the same pH.

6. The process according to claim 5, characterized in that in step a), the pH of the aqueous solution containing high molecular weight hyaluronic acid is adjusted to a value in the range from 2.3 to 2.7 and then the solution is diafiltered at the same pH.

7. The process according to claim 1, characterized in that in step a), the pH of the aqueous solution containing high molecular weight hyaluronic acid is adjusted by means of an HCl aqueous solution.

8. The process according to claim 1, characterized in that the sterilization step c) is a filtering sterilization step.

9. The process according to claim 1, characterized in that the step c) of sterilization is followed by a step d) of freeze drying the sterilized solution to obtain a dry powder of hyaluronic acid or salt thereof.

10. The process according to claim 9, characterized in that the sterilized solution is concentrated before the freeze drying step.

11. The process according to claim 1, characterized in that step b) of removing cells is carried out after the diafiltration of step a).

12. The process according to claim 11, characterized in that in step a), the pH of the aqueous solution containing high molecular weight hyaluronic acid is adjusted to 2.5–2.6 and then the solution is diafiltered at the same pH.

13. The process according to claim 11, characterized in that the filter used for the diafiltration of step a) has a pore size of 0.2 $\mu$m.

14. The process according to claim 11, characterized in that in step a), the hyaluronic acid solution is diafiltered until the filtrate to discard has an optical density (OD) at a wavelength of 280 nm equal to or lower than 0.02.

15. The process according to claim 11, characterized in that the step b) of removing cells is a centrifugation step.

16. The process according to claim 15, characterized in that the centrifugation step comprises adjusting the pH of the diafiltered aqueous solution obtained in step a) to a pH in the range from 3.5 to 5.0 and centrifuging the diafiltered aqueous solution for obtaining a supernatant containing hyaluronic acid.

17. The process according to claim 16, characterized in that the pH of the diafiltered aqueous solution obtained is step a) is adjusted to 4.0.

18. The process according to claim 17, characterized in that the pH is adjusted by means of a NaOH aqueous solution.

19. The process according to claim 15, characterized in that the sterilization step c) is a filtering sterilization step comprising adjusting the pH of the supernatant obtained in the step b) of centrifugation to a value of 7 and filtering the supernatant through a filter having a pore size of 0.2 $\mu$m.

20. The process according to claim 19, characterized in that the pH is adjusted by means of a NaOH aqueous solution.

21. The process according to claim 1, characterized in that the step b) of removing cells is carried out before the step a).

22. The process according to claim 21, characterized in that the step b) of removing cells is a diafiltration step of removing cells.

23. The process according to claim 22, characterized in that the diafiltration step b) of removing cells comprises adjusting the pH of an aqueous solution containing high molecular weight hyaluronic acid from a biological source to a pH of 3.5 and then diafiltering the solution at the same pH using a filter having a pore size of 0.2 $\mu$m.

24. The process according to claim 23, characterized in that the pH is adjusted by means of a HCl aqueous solution.

25. The process according to claim 21, characterized in that the filter used for the diafiltration step a) has a pore size of 300,000 D nominal molecular weight cut-off.

26. The process according to claim 21, characterized in that in step a), the pH of the aqueous solution containing high molecular weight hyaluronic acid is adjusted to 2.4 and then the solution is diafiltered at the same pH.

27. The process according to claim 21, characterized in that the sterilization step c) is a filtering sterilization step comprising adjusting the pH of the aqueous solution obtained in the step a) of diafiltration to a value of 7 and filtering the aqueous solution through a filter having a pore size of 0.2 $\mu$m.

28. The process according to claim 27, characterized in that the pH is adjusted by means of a NaOH aqueous solution.

* * * * *